United States Patent [19]

Kato et al.

[11] Patent Number: 4,591,423

[45] Date of Patent: May 27, 1986

[54] OXYGEN SENSOR

[75] Inventors: Nobuhide Kato, Aichi; Takao Murase, Konan, both of Japan

[73] Assignee: NGK Insulators, Ltd., Japan

[21] Appl. No.: 709,801

[22] Filed: Mar. 8, 1985

[30] Foreign Application Priority Data

Mar. 16, 1984 [JP] Japan .............................. 59-38407[U]
Aug. 29, 1984 [JP] Japan ............................ 59-131505[U]

[51] Int. Cl.⁴ ..................... G01N 27/04; G01N 27/58
[52] U.S. Cl. .................................... 204/428; 204/426; 338/34
[58] Field of Search .............. 204/424, 425, 426, 427, 204/428, 429, 15; 324/425; 338/34; 73/23; 123/489; 60/276

[56] References Cited

U.S. PATENT DOCUMENTS

| | | | |
|---|---|---|---|
| 4,019,974 | 4/1977 | Weyl | 204/428 |
| 4,402,820 | 9/1983 | Sano et al. | 204/425 |
| 4,413,502 | 11/1983 | Ohta et al. | 73/23 |
| 4,505,807 | 3/1985 | Yamada | 204/425 |

Primary Examiner—G. L. Kaplan
Attorney, Agent, or Firm—Parkhurst & Oliff

[57] ABSTRACT

An oxyen sensor for determining an oxygen partial pressure of a measurement gas in a measurement-space, comprising (a) an elongate oxygen sensing element having an oxygen detecting portion adjacent to its one longitudinal end, (b) a first protective covering for protecting at least an end portion of the sensing element which is located within the measurement-space and exposed to the measurement gas and which includes the oxygen detecting portion; (c) a second protective covering for covering another portion of the sensing element which is not exposed to the measurement gas; and (d) a retainer housing for supporting the sensing element, and the first and second protective coverings such that the end portion of the sensing element having the detecting portion is located within the conduit. The first and second protective coverings consist of an integral protective tubing member which is supported by the retainer housing with fluid tightness therebetween and which accommodates the oxygen sensing element. The oxygen sensor may comprise an air-tight mass of an inorganic particulate material which fills a portion of a space defined by the periphery of the sensing element and the inner surface of the protective tubing member, over a predetermined length along the axis of the protective tubing member.

16 Claims, 9 Drawing Figures

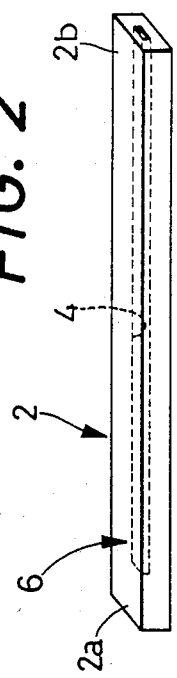
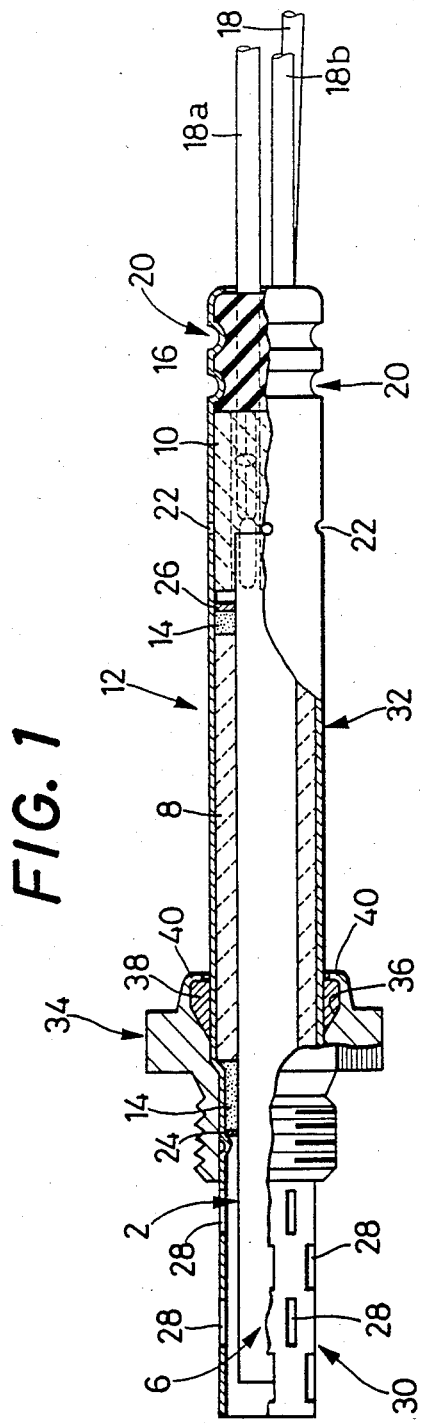
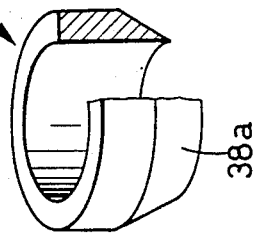

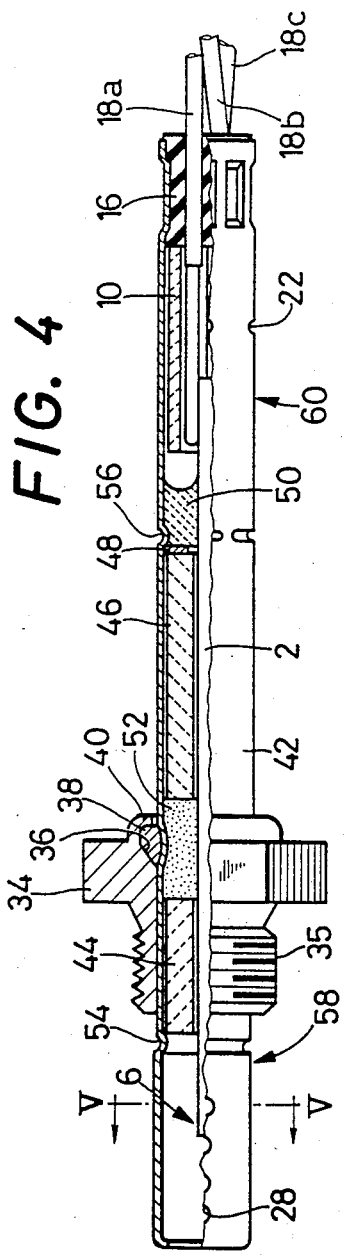
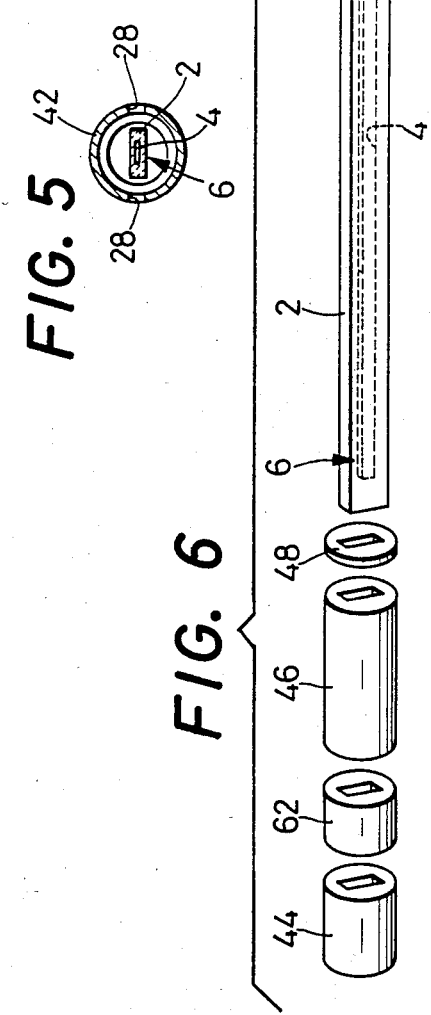

OXYGEN SENSOR

BACKGROUND OF THE INVENTION

The present invention relates generally to an oxygen sensor for detecting the oxygen concentration of a measurement gas, especially an exhaust gas produced by an internal combustion engine. More particularly, the invention is concerned with such an oxygen sensor which has an elongate sensing element having an oxygen detecting portion at its one end, and which is simple in construction and easy to manufacture and assemble.

There has been known an oxygen sensor which detects or determines the oxygen concentration of an exhaust gas emitted from internal combustion engines, for the purpose of controlling the combustion or fuel burning conditions of the engine according to signals produced by the oxygen sensor, and thereby purifying the exhaust gas and saving the fuel consumption of the engine. An example of such oxygen sensors uses a sensing element which comprises a body of oxygen-ion conductive solid electrolyte such as zirconium oxide doped with calcium oxide or yttrium oxide, and further comprises suitable electrodes disposed on opposite surfaces of the solid electrolyte body. In this oxygen sensor, one of the electrodes is exposed to a reference gas while the other electrode is exposed to the exhaust gas. In operation, the oxygen sensor produces an output signal which represents an electromotive force induced between the two electrodes according to the principle of an oxygen concentration cell. In recent years, there has been an increasing tendency to use an elongate planar sensing element rather than a conventionally used tubular sensing element, in view of ease of manufacture and structural simplicity of the sensor. Such an elongate planar sensing element has, at its one end, an oxygen detecting portion to be exposed to an exhaust gas or other measurement gas.

Oxygen sensors of various types as introduced above are installed such that their sensing element extends through the wall of a conduit through which an exhaust gas or other measurement gas is caused to flow, so that the end portion of the sensing element is inserted into the conduit and its detecting portion is exposed to the measurement gas in the measurement-space in the conduit. Generally, the oxygen sensor employs a first protective covering member, usually of cylindrical shape in cross section, which encloses the periphery of the end portion of the sensing element inserted in the fluid conduit, in order to protect the sensing element against thermal shock by high-temperature exhaust gas, to prevent particles in the exhaust gas from being deposited on the sensing element, and for other protective purposes. The oxygen sensor further employs a second protective covering member also of cylindrical shape which accommodates the exposed portion of the sensing element outside of the fluid conduit, in order to protect that exposed portion from outside foreign substances including liquids such as water.

In such a known oxygen sensor wherein the first and second protective covering members are separate parts, the structure for supporting various components of the sensor within the separate covering members is necessarily complicated, and accordingly the procedure to assemble the components into a sensor unit is cumbersome. In other words, an oxygen sensor using such separate protective covering member is relatively difficult to manufacture. In addition, the oxygen sensor is required to have complicated structures for attachment to the fluid conduit in such a manner as to ensure fluid-tight sealing at the first and second protective covering members, for preventing an exhaust gas or other measurement gas from leaking outside, and for protecting the sensor against entry of water or other liquids which would damage the sensing element as it operates at a high temperature. This sealing structure will lead to increased difficulty in the manufacture and assembling of the oxygen sensor.

SUMMARY OF THE INVENTION

The instant invention, therefore, has as its object the provision of an improved oxygen sensor for measuring or determining oxygen partial pressure of a measurement gas, which is simple in construction and easy to manufacture and assemble.

According to the invention, there is provided an oxygen sensor for determining an oxygen partial pressure of a measurement gas in a measurement-space, which comprises (a) an elongate oxygen sensing element having an oxygen detecting portion adjacent to one longitudinal end thereof; (b) first protective covering means for protecting at least an end portion of the sensing element which is located within the measurement-space and exposed to the measurement gas and which includes the oxygen detecting portion; (c) second protective covering means for covering another portion of the sensing element which is not exposed to the measurement gas; and (d) a retainer housing for supporting the sensing element, and the first and second protective covering means such that said end portion of the sensing element is located within the measurement-space, said first and second protective covering means consisting of an integral protective tubing member which is supported by the retainer housing with fluid tightness therebetween, the protective tubing member accommodating therein the oxygen sensing element.

According to one embodiment of the invention, the oxygen sensor further comprises an air-tight mass of an inorganic particulate material which fills a portion of a space defined by the periphery of the sensing element and the inner surface of the protective tubing member, over a predetermined length along the axis of the protective tubing member. This air-tight mass of inorganic particulate material may consist of talc.

In accordance with another embodiment of the invention, the oxygen sensor further comprises an air-tight sealing ring which is interposed between the outer surface of the protective tubing member and the retainer housing so as to maintain fluid tightness therebetween. In this case, it is preferred that a difference in coefficient of thermal expansion between any two members of the protective tubing member, air-tight sealing ring and the retainer housing be not greater than $3 \times 10^{-6}$ °C.$^{-1}$. Further, it is desired that the air-tight mass in the protective tubing member be positioned opposite to the air-tight sealing ring via a wall of the protective tubing member.

The previously indicated air-tight mass may be provided within the protective tubing member, at two or more positions which are spaced apart from each other along the axis or length of the protective tubing member.

According to a further embodiment of the invention, the sensing element is fixed within the protective tubing member at least at one position, with a suitable inorganic bonding agent such as cement or glass.

The protective tubing member may be formed from a single tubular member, e.g., a pipe, so as to provide a first portion serving as the first protective covering means, and a second portion serving as the second protective covering means. The first portion may be formed so as to have a smaller diameter than the second portion.

Alternatively, the protective tubing member may be produced by joining two separate tubular members into an integral member having portions serving as the first and second protective covering means, as with welding, calking or other suitable methods.

The sensing element may consist of an elongate plate-like member having a small width relative to its length. In one form of the oxygen sensor, at least the oxygen detecting portion of the sensing element is made of a solid electrolyte material which consists substantially of zirconia ceramics. According to another form of the oxygen sensor, the oxygen detecting portion is made substantially of an oxide semiconductor the electrical resistance of which is varied as a function of the oxygen partial pressure of the measurement gas. The oxygen sensor may comprise a heater to heat the oxygen detecting portion for more stability and accuracy of oxygen detecting operation.

BRIEF DESCRIPTION OF THE DRAWING

These and other objects, and many of the attendant features and advantages of this invention will be readily appreciated as the same becomes better understood by reference to the following detailed description of illustrative embodiments when considered in connection with the accompanying drawings, in which:

FIG. 1 is a partly cutaway view in longitudinal cross section of one embodiment of an oxygen sensor of the present invention;

FIG. 2 is a perspective view of an example of an oxygen sensing element used in the oxygen sensor of FIG. 1;

FIG. 3 is an perspective view of an air-tight sealing ring used in the oxygen sensor according to FIG. 1;

FIG. 4 is a view corresponding to FIG. 1, illustrating another embodiment of the oxygen sensor of the invention;

FIG. 5 is a schematic view in transverse cross section taken along line V—V of FIG. 4;

FIG. 6 is an exploded view of an oxygen sensing element and other parts of the oxygen sensor of FIG. 4, indicating the manner of assembling thereof;

DETAILED DESCRIPTION OF THE PREFERRED EMBODIMENT

Figure 7A:
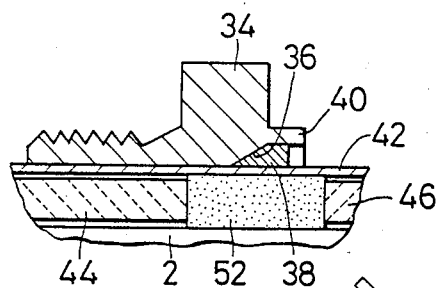
FIG. 7(a) is a fragmentary view in cross section, showing a metallic housing for supporting the oxygen sensor of FIG. 4 at its protective covering member, and related parts of the sensor, before the covering member is finally secured to the metallic housing.
Figure 7B:
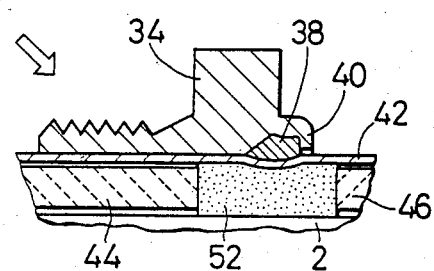
FIG. 7(b) is a view similar to FIG. 7(a) after the covering member has been finally secured to the metallic housing.

To further clarify the present invention, illustrative embodiments of the invention will be described in detail with reference to the accompanying drawing.

There is shown in FIG. 1 an oxygen sensor embodying the invention, which comprises an elongate planar oxygen sensing element of laminar structure generally indicated at 2. The planar sensing element 2 is formed of zirconia ceramics or other oxygen-ion conductive solid electrolyte materials. As illustrated in a perspective view of FIG. 2, the sensing element 2 is an elongate body of rectangular shape in transverse cross section having a small width relative to its length. The sensing element 2 has a reference-gas passage 4 which is formed therein along the length of the elongate body. The reference-gas passage 4 terminates at a first end portion 2a (left-hand side end as viewed in FIG. 2) of the elongate body of the sensing element 2, and is held in communication with an ambient atmosphere which serves as a reference gas used for the sensor.

As is well known, the oxygen sensing element 2 has an outer electrode (not shown) which is disposed at the first end portion 2a such that it is exposed to an exhaust gas or other gases that are measured by the instant oxygen sensor. In the meantime, an inner electrode (not shown) is disposed in a portion of the sensing element 2 substantially in alignment with the outer electrode, such that the inner electrode is exposed to the reference gas in the reference-gas passage 4. In this specific embodiment, the first end portion 2a of the sensing element 2 at which the outer and inner electrodes are disposed, forms an oxygen detecting portion 6 (FIG. 2) of the element 2. Suitable conductive leads extend from these outer and inner electrodes toward a second end portion 2b (right-hand side end as seen in FIG. 2) of th sensing element 2, whereby electric signals from the electrodes are fed to an external device.

The sensing element 2 incorporates a suitable electrical heater, as known in the art, which heats the oxygen detecting portion 6 of the sensing element 2 at which the electrodes are disposed. The heating of the detecting portion by the heater makes it possible to reduce the required warming-up time before the sensor becomes stably operative after the start of exposure to the measurement gas such as an exhaust gas (e.g., after the start of a cold engine whose exhaust gas is detected by the sensor). Further, the heater maintains the first end portion 2a (detecting portion 6) of the sensing element 2 at a desired temperature above a lower limit, even while the temperature of the measurement gas (e.g., exhaust gas) is not sufficiently high for intended operation of the sensor. Accordingly, the heater permits the oxygen sensor to achieve stable and accurate measurement of an oxygen concentration of the measurement gas at any time.

The sensing element 2 is produced in a suitable known manner, for example by laminating on a green sheet layers of the electrodes and heater, and other layers such as insulating layers, and co-firing the multi-layer laminar structure. Alternatively, the sensing element 2 is manufactured by forming the above indicated layers on the green sheet with a printing method, and co-firing the printed multi-layer structure. While the sensing element 2 preferably has an elongate plate-like configuration with a smaller width relative to its length, it may take other forms as long as they are generally elongate.

The elongate planar or plate-like sensing element 2 having the oxygen detecting portion 6 adjacent to its first or inner end portion 2a is supported at its intermediate portion by a first ceramic insulating member 8, and at its second end portion 2b by a second ceramic insulating member 10. These first and second ceramic insulating members 8, 10 are accommodated in a cylindrical protective tubing member 12 made of metal, and are fixed therein by fillers 14, 14 made of cement or other suitable bonding materials, which are provided at opposite longitudinal ends of the first ceramic insulating member 8. The fillers 14 separate the interior of the protective tubing member 12 into plural spaces in mutually fluid-tight or air-tight condition. The sensing element 2 is positioned such that its oxygen detecting portion 6 is disposed in the space formed in one end portion (left-hand side end portion as seen in FIG. 1) of the protective tubing member 12 corresponding to the first or inner end portion 2a of the sensing element 2, and such that the reference-gas passage 4 is open in the space formed in the second or outer end portion (right-hand side end portion as viewed in FIG. 1) of the protective tubing member 12.

A rubber plug 16 is press-fitted in the second end portion of the protective tubing member 12. Electrically conductive members in the form of lead wires 18a, 18b and 18c extend through the rubber plug 16 into the second ceramic insulating member 10. Plural connectors (not shown) are supported in the insulating member 10 and are electrically connected to the lead wires 18a, 18b and 18c. With these connectors, the lead wire 18a is connected to a lead extending from the previously indicated inner electrode exposed to the reference gas in the passage 4, while the lead wires 18b and 18c are connected to a pair of electrical leads extending from the built-in heater, respectively. The outer electrode which is exposed to the measurement gas is connected through the corresponding connector to the protective tubing member 12, and is grounded through a metallic retainer housing 34 which is electrically connected to the protective tubing member 12 as described later.

The end portion of the protective tubing member 12 in which the rubber plug 16 is accommodated, is compressed or calked radially inwardly against the surface of the rubber plug 16, at two axially spaced-apart positions. As a result, two radially inwardly indented parts 20, 20 are formed on the end portion of the protective tubing member 12. These indented parts 20 compress the rubber plug 16 in the radially inward direction, thereby retaining the lead wires 18a, 18b and 18c firmly in the rubber plug 16, and preventing vibrational or rattling movements of these lead wires which would otherwise be transmitted to the associated components within the oxygen sensor, particularly to the electrical connections. Namely, the fatigue failure of the electrical connections is prevented by the compression pressure imparted to the rubber plug 16 by the indented parts 20 of the tubing member 12.

The second ceramic insulating member 10 is retained in position by the sensing element 2 whose second end portion 2b is inserted therein, and by the rubber plug 16. Since the open end of the protective tubing member 12 is air-tightly closed by the rubber plug 16, the cylindrical wall of the tubing member 12 has air-inlet apertures 22 through which the reference-gas passage 4 communicates with the ambient air outside the tubing member 12. Reference numerals 24, 26 designate retainer plates for the fillers 14, 14.

As is apparent from FIG. 1, the protective tubing member 12 accommodating therein the sensing element 2 has a small-diameter end portion 30 which serves as first protective covering means for protecting the portion of the sensing element 2 which includes the detecting portion 6. This small-diameter end portion 30 (i.e., the first protective covering means) is located within a measurement-space which is defined, in this specific embodiment, in a fluid conduit such as an exhaust pipe of a vehicle through which a measurement gas such as an exhaust gas flows. The detecting portion 6 of the sensing element 2 is disposed in the small-diameter end portion 30 of the tubing member 12, so that the detecting portion 6 is exposed to the measurement gas which is introduced through plural openings 28 formed through the wall of the small-diameter end portion 30. The protective tubing member 12 further has a large-diameter portion 32 which is larger in diameter than the small-diameter end portion 30. The tubing member 12 extends through the previously indicated metallic retainer housing 34 so that the retainer housing 34 supports the tubing member 12 at a portion thereof which includes the jointing parts of the large-diameter portion 32 and the small-diameter end portion 30. The large-diameter portion 32 serves as second protective covering means for covering the portion of the sensing element 2 which is located outside the retainer housing 34 and the fluid conduit, that is, for protecting the portion of the element 2 which is not exposed to the measurement gas. The protective tubing member 12 is formed from a single tubular member, e.g., a pipe so as to provide an integral tubular member consisting of the small-diameter end portion 30 (first protective covering means) and the large-diameter portion (second protective covering means).

The retainer housing 34 is threaded for example to a fluid conduit such that the small-diameter end portion 30 of the tubing member 12 is disposed within the fluid conduit with fluid tightness between the retainer housing 34 and the wall of the fluid conduit, and between the tubing member 12 and the retainer housing 34.

Described in more detail, the retainer housing 34 has an annular recess 36 in a rear part (on the side remote from the threaded end) of its inner surface defining a bore through which the tubing member 12 extends. This annular recess 36 and the outer surface of the tubing member 12 cooperate to define a sealing space in which there is disposed an air-tight sealing ring 38 as illustrated in FIG. 3, such that its wedged end 38a is positioned on the inner side of the annular recess 36 longitudinally of the tubing member 12. This inner wedged end 38a of the sealing ring 38 serves to fill a gap between the inner surface of the retainer housing 34 and the outer surface of the tubing member 12, thereby maintaining air tightness between these two members 34, 12. The sealing ring 38 interposed between the retainer housing 34 and the tubing member 12 is retained within the sealing space (36) by calking the rear end portion of a cylindrical flange 40 of the retainer housing 34 against the outer end face of the sealing ring 38.

In the oxygen sensor constructed as described heretofore, the inner electrode disposed at the detecting portion 6 of the sensing element 2 is exposed to the ambient air in the reference-gas passage 4, which is introduced through the air-inlet apertures 22. On the other hand, the outer electrode also disposed at the detecting portion 6 is exposed to the measurement gas, e.g., engine exhaust gas flowing through the exhaust pipe, which is introduced through the openings 28. In this arrangement, an output electrical signal indicative of the oxygen concentration of the measurement gas is obtained between the lead wire 18a connected to the inner electrode, and the grounded outer electrode.

As discussed heretofore, the instant oxygen sensor uses the integral protective tubing member 12 which has the small-diameter end portion 30 for covering the portion of the sensing element 2 located within the fluid conduit, and the large-diameter portion 32 for covering the portion of the element 2 located outside the retainer housing 34. Unlike a known covering arrangement which consists of two separate covering members for two distinct portions of the sensing element 2, the instant one-piece or integral protective covering member, i.e., tubing member 12 according to this embodiment of the invention makes it possible to simplify the overall construction of the oxygen sensor to a greatly appreciable extent, and consequently provides for easy manufacture, assembling and installation of the oxygen sensor. The ease of assembling and installation is appreciated in a comparatively higher degree, especially when the oxygen sensor uses a sensing element of elongate plate-like configuration, like the element 2 of the instant illustrated embodiment. In this case, the sensing element 2 is set in position within the one-piece protective tubing member 12, and a unitary sub-assembly of these two members 2, 12 is easily attached to the retainer housing 34 which has been threaded to the fluid conduit.

In attaching the tubing member 12 to the retainer housing 34, it is necessary to maintain air tightness between these members to prevent leakage of the measurement gas through the gap therebetween. For this purpose, several methods are available, such as press-fit, soldering and welding. However, the use of an air-tight sealing ring with a wedged end, as indicated at 38 in the illustrated embodiment, is most recommended as simple and reliable means for sealing the protective tubing member 12 and the retainer housing 34.

As previously stated, the tubing member 12 used in the illustrated embodiment is manufactured by forming a single tubular workpiece so as to provide the small-diameter end portion 30 as the first protective covering means, and the large-diameter portion 32 as the second protective covering means. That is, the manufacture of the tubing member 12 is extremely easy and simple. However, the tubing member 12 may be produced by joining, as with welding or calking, two separate tubular members which have been pre-formed to serve as the small-diameter end portion 30 and the large-diameter portion 32, respectively.

Referring now to FIGS. 4 through 8, another embodiment of the oxygen sensor of the present invention will be described. In the figures, the same reference numerals as used in FIGS. 1–3 will be used to identify parts which are similar to the corresponding parts of the preceding embodiment of FIGS. 1–3. In the interest of brevity and simplification, the following description of this modified embodiment refers only to such parts of the oxygen sensor that are modified with respect to the preceding embodiment, and repeated description of those parts will not be provided.

The oxygen sensor according to this embodiment is shown in FIG. 4, wherein a protective tubing member 42 accommodates therein a first ceramic insulating member 44 and a second ceramic insulating member 46 which are spaced apart from each other in the longitudinal direction of the tubing member 42. These first and second insulating members 44, 46 support the plate-like sensing element 2 at its longitudinally spaced-apart portions, respectively, i.e., at a portion located within the retainer housing 34, and at an intermediate portion outside the retainer housing 34. It is noted that the insulating member 10, which is referred to as "second insulating member", is used in the present embodiment as a third insulating member for electrical connection of the sensor. The sensing element 2 is fixed in the tubing member 42 by a bonding mass 50 of a suitable bonding agent, and an air-tight mass 52 of an inorganic particulate material which will be described in greater detail. The bonding mass 50 is held in pressed contact with a washer 48 which is disposed in contact with the rear end of the second insulating member 46. The air-tight mass 52 is disposed over a suitable length along the axis of the tubing member, so as to fill a space which is defined by the inner surface of the tubing member 42, the periphery of the sensing element 2, the rear end of the first insulating member 44 and the front end of the second insulating member 46. In this arrangement, a front space in the tubing member 42 in which the detecting portion 6 of the sensing element 2 is located, is air-tightly separated by the air-tight mass 52 from a rear space with which the reference-gas passage 4 of the sensing element 2 communicates at its open end remote from the detecting portion 6. The tubing member 42 is radially inwardly compressed at two longitudinally spaced-apart portions thereof so as to provide a first and a second radially inward protrusion 54, 56 as shown in FIG. 4. These inward protrusions 54, 56 prevent the first insulating member 44, air-tight mass 52, second insulating member 46 and washer 48 from moving within the tubing member 42 in the longitudinal direction.

In this modified embodiment, a portion of the tubing member 42 having the previously indicated openings 28 (FIGS. 4 and 5), more precisely, a front end portion extending forwardly from the air-tight mass 52 serves as a first protective covering portion 58 which corresponds to small-diameter end portion 30 of the preceding embodiment. On the other hand, a portion of the tubing member 42 which extends rearwardly from the air-tight mass 52 serves as a second protective covering portion 60 corresponding to the large-diameter portion 32 of the preceding embodiment. The tubing member 42 having these two covering portions 58, 60 is supported by the retainer housing 34 which is threaded at 35 to an exhaust pipe or other means defining a measurement-space in which the measurement gas is present.

The air-tight mass 52 used in the illustrated modified embodiment is press-formed by compression of particles of heat-resistant inorganic materials such as talc and alumina, while the bonding mass 50 is formed of a suitable inorganic bonding agent such as glass. The use of inorganic particulate material with high heat-resistance (not lower than 500° C. in general, but depending upon operating environments of the sensor) permits the air-tight mass 52 to maintain the intended air tightness for a relatively longer period of time even if the air-tight mass 52 is alternately heated and cooled periodically. Similarly, the use of inorganic bonding agent for the bonding mass 56 assures stable support and fixation of the sensing element 2 within the tubing member 42.

To fix the sensing element 2 within the protective tubing member 42, the sensing element 2 is passed through the first and second ceramic insulating members 44, 46 and washer 48, and through a press-molded article 62, as shown in FIG. 6. The article 62, which eventually serves as the air-tight mass 52, is press-molded of particles of talc or other inorganic material with a relatively low density. In the meantime, the tubing member 42 is prepared with only the first inward protrusion 54, viz., without the second inward protrusion 56 which is formed subsequently.

The assembly of the first insulating member 44, press-molded article 62, second insulating member 46, washer 48, and sensing element 2 is inserted into the protective tubing member 42 through the opening at the rear or outer end on the side of the rubber plug 16, while the tubing member 42 is supported in its upright posture with a suitable fixture, such that the rear end is open upward. The inserted assembly is stopped and positioned by the first inward protrusion 54 when the lower edge of the first insulating member 44 is brought into abutment with the protrusion 54. At the same time, the sensing element 2 is positioned by the fixture supporting the tubing member 42.

In this condition, the washer 48 is pressed against the upper end face of the second insulating member 46, with a suitable tool, whereby the low-density press-molded article 56 is further compressed and deformed into the air-tight mass 52 having an increased density. Thus, the air-tight mass 52 fills the space defined by the tubing member 42, sensing element 2, and first and second insulating members 44, 46. With the pressure exerted on the washer 48, the tubing member 42 is radially inwardly compressed to form the second inward protrusion 56 which holds the inserted assembly in position.

After the sensing element 2 has been positioned and fixed in the tubing member 42, and the air-tight mass 52 has been formed, a suitably pre-formed mass of glass is inserted into the tubing member 42 and fused into the bonding mass 50.

The retainer housing 34 is mounted on the protective tubing member 42, so that the retainer housing 34 is positioned longitudinally of the tubing member 42 so as to substantially cover a portion of the latter in which the air-tight mass 52 is disposed. Described more specifically referring to FIGS. 7(a) and 7(b), the cylindrical flange 40 of the retainer housing 34 is calked against the sealing ring 38 positioned in the sealing space (annular recess) 36, whereby the retainer housing 34 is secured to the tubing member 42. The calking action on the cylindrical flange 40 causes the sealing ring 38 to force the corresponding part of the cylindrical wall of the tubing member 42 radially inwardly against the air-tight mass 52, and consequently causes that part of the wall to be inwardly protruded. Since the volume of the space accommodating the air-tight mass 52 is fixed by the defining surfaces of the first and second insulating members 44, 46, tubing member 42 and sensing element 2, the inward protrusion of the cylindrical wall of the tubing member 42 results in further compression of the particles of the air-tight mass 52 and accordingly increases the density or air tightness of the air-tight mass 52. In addition, the reaction force of the air-tight mass 52 acts to increase the surface pressure between the tubing member 42 and the sealing ring 38, and therefore improves the air-tightness between the tubing member 42 and the retainer housing 34.

The protective tubing member 42 used in this second embodiment is made of stainless steel SUS-310S having an average coefficient of thermal expansion of $17.5 \times 10^{-6}$° C.$^{-1}$ at 0°–600° C. The retainer housing 34 and the sealing ring 38 are made of stainless steel SUS-304 with an average coefficient of thermal expansion of $18.9 \times 10^{-6}$° C.$^{-1}$ at 0°–600° C. As indicated above, the difference in thermal expansion coefficient between any two of the three members 42, 34, 38 is held relatively small for increased air tightness between the retainer 34 and the tubing member 42. In other words, the use of materials whose thermal expansion coefficients differ from each other in a large degree would cause a relative large gap to be present between the retainer housing 34 and the tubing member 42 after a long period of service of the oxygen sensor under varying temperatures. For improved air tightness between the retainer housing 34 and the tubing member 42, it is recommended to use metallic materials whose difference in thermal expansion coefficient is not greater than $3 \times 10^{-6}$° C.$^{-1}$.

While the bonding mass 50 for fixing the sensing element 2 to the tubing member 42 is formed of glass, it is possible to use other inorganic bonding agents such as a cement. This bonding mass 50 may be provided at two or more positions which are spaced apart from each other in the longitudinal direction of the tubing member 42.

Although the air-tight mass 52 is preferably made of particles of talc as in the preceding embodiment, other heat-resistant inorganic particulate materials such as particles of alumina may be used. Further, it is possible to provide the air-tight mass 52 at plural positions which are spaced apart from each other in the longitudinal direction of the tubing member 42. In this case, one of the air-tight masses (52) which is disposed in the second protective covering portion 60 may function as the bonding mass 50, or replace the bonding mass 50, so as to fix the sensing element 2 to the tubing member 42.

Figure 8:
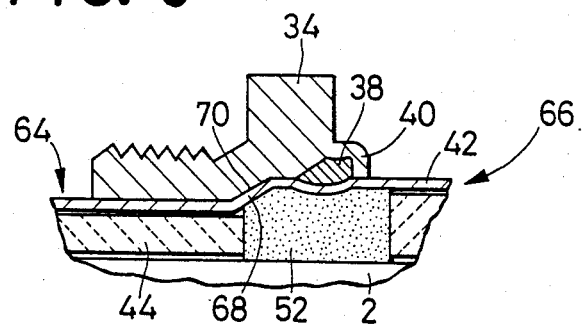
FIG. 8 is a fragmentary cross sectional view corresponding to FIG. 7(b), showing a further embodiment of the invention.

While the protective tubing member 42 has the same diameter over the entire length, it is appreciated that the tubing member 42 be formed from a two-diameter pipe which has small-diameter end portion 64 (corresponding to the portion 30 of the first embodiment of FIG. 1), a large-diameter portion 66 (corresponding to the portion 32 of the first embodiment), and a tapered portion 68 connecting the portions 64 and 66, as depicted in FIG. 8. In this case, the tubing member 42 is easily and suitably clamped by a fixture when the press-molded article 62 in the tubing member 42 is compressed into the air-tight mass 52 during the assembly of the oxygen sensor. In other words, the use of such a two-diameter pipe makes it possible to avoid buckling or other troubles with the tubing member 42. which would take place if the tubing member 42 is clamped at its end portion during the assembly of the sensor. Further, the two-diameter pipe permits its tapered portion 68 to snugly fit the mating inner surface 70 of the retainer housing 34, thereby assuring better air-tight sealing between the two members 34 and 42.

While the present invention has been described in its preferred embodiments for illustrative purpose, it is to be understood that the invention is not confined to the disclosed details, and that many changes and modifications may be made therein.

For example, although it is preferred to form the sensing element 2 of a solid electrolyte which consists substantially of zirconia ceramics, it is possible to use other solid electrolyte materials.

Further, the oxygen detecting portion 6 of the sensing element 2 may be formed substantially of an oxide semi-conductor such as titanium oxide whose electrical resistance is varied as a function of an oxygen concentration of a measurement gas such as an exhaust gas. In this instance, the oxygen sensor detects a variation in the electrical resistance of the detecting portion 6 which is caused by a variation in the oxygen partial pressure of the measurement gas.

It will be obvious to those skilled in the art that various other changes, modifications and improvements are possible without departing from the scope of the invention defined in the appended claims.

What is claimed is:

1. An oxygen sensor for determining an oxygen partial pressure of a measurement gas in a measurement-space, comprising:
   an elongate oxygen sensing element having an oxygen detecting portion adjacent to one longitudinal end thereof;
   first protective covering means for protecting at least an end portion of said sensing element which is located within said measurement-space and exposed to said measurement gas, said sensing element including said oxygen detecting portion;
   second protective covering means for covering a portion of said sensing element which is not exposed to said measurement gas;
   a retainer housing for supporting said sensing element, said first protective covering means and said second protective covering means such that said end portion of the sensing element is located within said measurement-space, said retainer housing having a bore formed therethrough;
   said first and second protective covering means consisting of an integral protective tubing member which is supported by said retainer housing, said protective tubing member extending through said bore of the retainer housing and accommodating said oxygen sensing element; and
   an air-tight metallic sealing ring interposed between an outer surface of said protective tubing member and an inner surface of said retainer housing which defines a portion of said bore, providing for fluid tightness therebetween.

2. The oxygen sensor of claim 1, further comprising an air-tight mass of an inorganic particulate material which fills a portion of a space defined between an outer peripheral portion of said sensing element and an inner surface of said protective tubing member, over a predetermined length along the axis of said protective tubing member.

3. The oxygen sensor of claim 2, wherein said mass of inorganic particulate material consists essentially of talc.

4. The oxygen sensor of claim 2, wherein said air-tight mass is provided within said protective tubing member, at a plurality of positions which are spaced apart from each other along the axis of said protective tubing member.

5. The oxygen sensor of claim 1, wherein a difference in the coefficient of thermal expansion between any two members of said protective tubing member, said air-tight sealing ring and said retainer housing, is not greater than $3 \times 10^{-6}$ °C.$^{-1}$.

6. The oxygen sensor of claim 1, wherein said air-tight mass in said protective tubing member is positioned opposite to said air-tight sealing ring via a wall of said protective tubing member.

7. The oxygen sensor of claim 1, wherein said sensing element is fixed within said protective tubing member at least at one position, with a bonding agent selected from the group of inorganic materials consisting of cement and glass.

8. The oxygen sensor of claim 1, wherein said protective tubing member consists of a pipe having a small-diameter portion and a large-diameter portion.

9. The oxygen sensor of claim 1, wherein said sensing element consists of an elongate plate-like member having a small width relative to its length.

10. The oxygen sensor of claim 1, wherein at least said oxygen detecting portion of said sensing element comprises a solid electrolyte material consisting essentially of zirconia ceramics.

11. The oxygen sensor of claim 1, wherein said oxygen detecting portion of said sensing element consists essentially of an oxide semiconductor, which has an electrical resistance which varies as a function of oxygen partial pressure of the measurement gas.

12. The oxygen sensor of claim 1, wherein said protective tubing member is formed from a single tubular member to provide a first portion serving as said first protective covering means, and a second portion serving as said second protective covering means.

13. The oxygen sensor of claim 12, wherein said protective tubing member is produced by joining two separate members into an integral member having said first and second protective covering means.

14. The oxygen sensor of claim 1, wherein said sensing element comprises a heater incorporated therein to heat said oxygen detecting portion.

15. An oxygen sensor for determining an oxygen partial pressure of a measurement gas in a measurement-space, comprising:
   an elongate oxygen sensing element having an oxygen detecting portion adjacent to one longitudinal end thereof;
   first protective covering means for protecting at least an end portion of said sensing element which is located within said measurement-gas space and exposed to said measurement gas, said sensing element including said oxygen detecting portion;
   second protective covering means for covering a portion of said sensing element which is not exposed to said measurement gas;
   a retainer housing for supporting said sensing element, said first protective covering means and said second protective covering means such that said end portion of the sensing element is located within said measurement-space, said retainer housing having a bore formed therethrough;
   said first and second protective covering means consisting of an integral protective tubing member which is formed from a single tubular member and which is supported by said retainer housing, said protective tubing member accommodating said oxygen sensor element;
   an air-tight mass of an inorangic particulate material which fills a portion of a space defined between an outer peripheral portion of said sensing element and an inner surface of said protective tubing member, over a predetermined length along the axis of said protective tubing member; and
   an air-tight metallic sealing ring interposed between an outer surface of said protective tubing member and an inner surface of said retainer housing which defines a portion of said bore, so as to prevent said measurement gas in said measurement-space from leaking between said sealing ring and said protective tubing member, and between said sealing ring and said retainer housing, said air-tight mass in said protective tubing member being positioned opposite to said air-tight sealing ring via a wall of said protective tubing member.

16. An oxygen sensor for determining an oxygen partial pressure of a measurement gas in a measurement-space, comprising:

an elongate oxygen sensing element having an oxygen detecting portion adjacent to one longitudinal end thereof;

first protective covering means for protecting at least an end portion of said sensing element which is located within said measurement-gas space and exposed to said measurement gas; said sensing element including said oxygen detecting portion;

second protective covering means for covering a portion of said sensing element which is not exposed to said measurement gas;

a retainer housing for supporting said sensing element, said first protective covering means and said second protective covering means such that said end portion of the sensing element is located within said measurement-space, said retainer housing having a bore formed therethrough; and said first and second protective covering means consisting of an integral protective tubing member which is formed from a single tubular member and which is supported by said retainer housing, said protective tubing member extending through said bore of the retainer housing with additional means to provide fluid tightness therebetween and accommodating said oxygen sensor element in said protective tubing member.

* * * * *